US009937239B2

(12) United States Patent
Karig

(10) Patent No.: US 9,937,239 B2
(45) Date of Patent: Apr. 10, 2018

(54) PRESERVATION AND RECONSTITUTION OF CELL-FREE PROTEIN EXPRESSION SYSTEMS

(71) Applicant: The Johns Hopkins University, Baltimore, MD (US)

(72) Inventor: David K. Karig, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/697,797

(22) Filed: Apr. 28, 2015

(65) Prior Publication Data

US 2015/0335718 A1    Nov. 26, 2015

Related U.S. Application Data

(60) Provisional application No. 62/001,198, filed on May 21, 2014.

(51) Int. Cl.
| | | |
|---|---|---|
| *A61K 38/00* | (2006.01) | |
| *A61K 38/45* | (2006.01) | |
| *A61K 35/74* | (2015.01) | |
| *A61K 36/18* | (2006.01) | |
| *A61K 36/06* | (2006.01) | |
| *A61K 35/12* | (2015.01) | |
| *C09K 3/00* | (2006.01) | |
| *A61K 36/899* | (2006.01) | |
| *A61K 36/064* | (2006.01) | |
| *A61K 35/63* | (2015.01) | |

(52) U.S. Cl.
CPC .............. *A61K 38/45* (2013.01); *A61K 35/12* (2013.01); *A61K 35/63* (2015.01); *A61K 35/74* (2013.01); *A61K 36/06* (2013.01); *A61K 36/064* (2013.01); *A61K 36/18* (2013.01); *A61K 36/899* (2013.01); *C09K 3/00* (2013.01); *C12Y 207/03002* (2013.01)

(58) Field of Classification Search
None
See application file for complete search history.

(56) References Cited

U.S. PATENT DOCUMENTS

| | | | |
|---|---|---|---|
| 7,048,915 B2 | 5/2006 | Kuroita et al. | |
| 7,399,610 B2 | 7/2008 | Shikata et al. | |
| 8,921,085 B2 * | 12/2014 | Battrell | C12Q 1/6806 435/188 |
| 2002/0039771 A1 | 4/2002 | Peters et al. | |
| 2007/0128633 A1 | 6/2007 | Zozulya et al. | |
| 2008/0076905 A1 | 3/2008 | Yokoyama et al. | |
| 2011/0020925 A1 | 1/2011 | Bauzon et al. | |
| 2012/0088269 A1 | 4/2012 | Kusumegi et al. | |
| 2012/0114646 A1 | 5/2012 | Tchessalov et al. | |
| 2014/0295492 A1 | 10/2014 | Jewett et al. | |
| 2016/0312312 A1 | 10/2016 | Pardee et al. | |

FOREIGN PATENT DOCUMENTS

WO     2007/148092     12/2007

OTHER PUBLICATIONS

Sitaraman et al. Chapter 15. "High-Throughput protein expression using cell-free system", p. 229-244, from High Throughput Protein Expression and Purification, 2009, Humana Press, Edited by Sharon A. Doyle.*
Kigawa et al., Journal of Structural and Functional Genomics, 2004, vol. 5, p. 63-68.*
Mark Thomas Smith et al., "Lyophilized *Escherichia coli*-based cell-free systems for robust, high-density, long-term storage," BioTechniques vol. 56 No. 4, pp. 186-193 (Apr. 2014).
Alexander S. Spirin and James R. Swartz, "Cell-Free Protein Synthesis Methods and Protocols", Wiley-VCH Verlag GmbH & Co., KGaA, 2008, pp. 1-35.
Pardee et al., "Paper-Based Synthetic Gene Networks," Cell 159, Nov. 6, 2014, Elsevier, Inc., pp. 940-954.
Pardee et al., "Portable, On-Demand Biomolecular Manufacturing," Cell 167, Sep. 22, 2016, Elsevier, Inc., pp. 248-259.
Smith et al., "Creating a Completely 'Cell-free' System for Protein Synthesis," Biotechnol. Prog., 2015, vol. 31, No. 6, American Institute of Chemical Engineers, Aug. 28, 2015, pp. 1716-1719.
Salehi et al., "Cell-free Protein Synthesis of a Cytotoxic Cancer Therapeutic Onconase Production and a Just-add-water Cell-free System," Biotechnol. J. 2016, 11, 274-281, Wiley-VCH Verlag GmgH & Co., Sep. 18, 2015.

* cited by examiner

*Primary Examiner* — Kade Ariani
(74) *Attorney, Agent, or Firm* — Todd R. Farnsworth

(57) ABSTRACT

A method of preserving a cell-free protein expression system includes preserving a cell extract with a first non-reducing sugar alcohol to provide a preserved cell extract, preserving a reaction buffer with a second non-reducing sugar alcohol to provide a preserved reaction buffer, and preserving an energy source, so that the cell extract, the reaction buffer, and the energy source are preserved separately.

13 Claims, 12 Drawing Sheets

US 9,937,239 B2

PRESERVATION AND RECONSTITUTION OF CELL-FREE PROTEIN EXPRESSION SYSTEMS

CROSS-REFERENCE TO RELATED APPLICATIONS

This application claims the benefit of U.S. Provisional Application No. 62/001,198 filed on May 21, 2014, the entire contents of which are hereby incorporated herein by reference.

TECHNICAL FIELD

Example embodiments relate generally to methods of preserving cell-free protein expression systems.

BACKGROUND

Cell-free protein expression systems have found widespread use in protein purification, basic research, drug production, and screening. However, many potential applications are limited by the need for cold chain storage. In particular, reagents for cell-free protein expression are typically stored at freezing temperatures. Accordingly, current approaches are not available for the preservation of cell-free protein expression systems at elevated temperatures or even at ambient temperatures without oxygen and/or humidity control. Additionally, current approaches for preservation of cell-free protein expression systems do not demonstrate long term stability (particularly under heat stress), scalability, or production of proteins capable of performing both transcription and translation.

Therefore there remains a need in the art for a method of preserving a cell-free protein expression system in a manner that it can be stored, even under heat stress and without oxygen or humidity control, can be later reconstituted on demand, and results in long term stability, scalability, and production of proteins capable of performing both transcription and translation.

BRIEF SUMMARY

One or more embodiments of the invention may address one or more of the aforementioned problems. Certain embodiments according to the present invention provide a method of preserving a cell-free protein expression system suitable for a wide variety of applications. In accordance with certain embodiments, the method may comprise preserving a cell extract with a first non-reducing sugar alcohol to provide a preserved cell extract, preserving a reaction buffer with a second non-reducing sugar alcohol to provide a preserved reaction buffer, and preserving an energy source, so that the cell extract, the reaction buffer, and the energy source are preserved separately.

BRIEF DESCRIPTION OF THE DRAWING(S)

Example embodiments of the present invention now will be described more fully hereinafter with reference to the accompanying drawings, in which some, but not all embodiments of the invention are shown. Indeed, this invention can be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Figure 1:
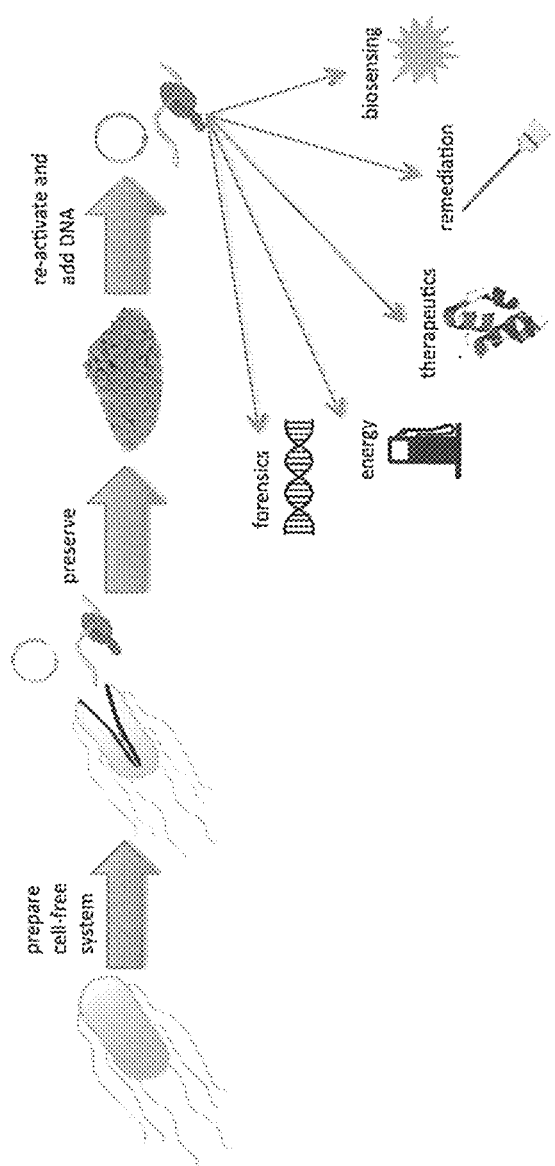
FIG. 1 illustrates an overview of cell-free protein expression system preservation according to an example embodiment.

Some example embodiments now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

An example embodiment includes a method of preserving a cell-free protein expression system suitable for a wide variety of applications. In accordance with certain embodiments, the method may comprise preserving a cell extract with a first non-reducing sugar alcohol to provide a preserved cell extract, preserving a reaction buffer with a second non-reducing sugar alcohol to provide a preserved reaction buffer, and preserving an energy source, so that the cell extract, the reaction buffer, and the energy source are preserved separately.

The term "cell-free protein expression system", as used herein, may comprise an in vitro means of implementing biological reactions that happen within cells while reducing the complex interactions found in a whole cell. To create cell-free systems, sub-cellular fractions may be isolated, for example, by lysis and ultracentrifugation to provide molecular machinery that can be used in reactions in the absence of many of the other cellular components. As used herein, the term "cell extract" may generally refer to these isolated sub-cellular fractions. Cell-free systems may also be prepared, for instance, by mixing a number of purified enzymes and coenzymes. Cell-free systems may be advantageous, for example, because very high product yields are usually accomplished without the formation of by-products or the synthesis of cell mass. Additionally, cell-free systems may be able to implement some biological reactions that living organisms cannot perform. Also, cell-free systems may have faster reaction rates than living systems since all energy resources may be devoted to producing the desired RNA or proteins. Furthermore, cell-free synthesis products do not need to traverse a cell membrane to be available for analysis or activity at a desired location.

The term "energy source", as used herein, may comprise any high-energy phosphate donor that donates a phosphate group to adenosine diphosphate (ADP) for the biosynthesis of adenosine triphosphate (ATP).

The term "expression construct", as used herein, may comprise a DNA molecule or set of molecules that codes for production of mRNA and/or protein in the presence of transcription and/or translation machinery. In some embodiments, for example, the DNA molecule or set of molecules may be in the form of a plasmid, a product of a polymerase chain reaction, a bacterial artificial chromosome, a chromosome, or fragments of chromosomal DNA. As an alternative to a DNA expression construct, an mRNA expression construct may be used that codes for production of protein in the presence of translation machinery.

The term "unregulated atmosphere", as used herein, may comprise a realistic, standard atmosphere without any oxygen control or humidity control.

In some example embodiments, a method of preserving a cell-free protein expression system having a wide variety of applications is provided. For instance, this method may provide, for example, on-demand biosensors (e.g., protein switches, antibodies, gene networks, etc.), on-demand therapeutics (e.g., protein therapeutics, vaccines, antibacterial peptides, antiviral peptides, etc.), facilitated shipping and distribution via weight reduction associated with drying and lack of need for cold chain storage (e.g., for environmental bioremediation), reduced commercial shipping costs, forensics (e.g., DNA polymerase for PCR), energy applications via sustained reactions from periodically purging spent expression reagents and reconstituting dried expression reagents in an automated fashion (e.g., fuel cell operation, generation of long chain hydrocarbons, etc.) and/or the like. In general, methods of preserving cell-free protein expression systems according to certain example embodiments may include preserving a cell extract with a first non-reducing sugar alcohol to provide a preserved cell extract, preserving a reaction buffer with a second non-reducing sugar alcohol to provide a preserved reaction buffer, and preserving an energy source, so that the cell extract, the reaction buffer, and the energy source are preserved separately. Surprisingly, by preserving the cell extract, the reaction buffer, and the energy source separately, the cell-free protein expression system may demonstrate pronounced improvements in stability. As such, rather than preserving individual proteins or cell products, biological machinery capable of synthesizing essentially any protein or cell product on demand may be preserved. Accordingly, preservation methods according to example embodiments may enable operation of entire gene networks following storage.

In accordance with an example embodiment, for instance, preserving the cell extract may comprise dissolving the first non-reducing sugar alcohol in the cell extract to provide a cell extract solution, manipulating the cell extract solution to prevent fouling, and drying the cell extract solution. In such embodiments, for example, manipulating the cell extract solution may comprise at least one of filtering the cell extract solution or adding an anti-fouling agent to the cell extract solution. In some embodiments, for instance, the anti-fouling agent may comprise an RNAse inhibitor, an antibiotic that does not interfere with transcription or translation, or any combination thereof. Determining which manipulation method to use may at least partially depend on the scalability necessary for the cell-free protein expression system preservation. For example, for smaller scale preservations, filtering the cell extract solution may be a suitable method. For larger scale preservations, however, adding an anti-fouling agent such as antibiotics may be a more suitable method.

According to certain embodiments, for instance, drying the cell extract solution may comprise drying small volume (e.g., 5 µL-35 µL) aliquots on, for example, a silicon sheet at 37° C. In other embodiments, for example, drying the cell extract solution may comprise freeze drying the cell extract solution. In further embodiments, for instance, drying the cell extract solution may comprise spray drying, spray freeze drying, or supercritical drying the cell extract solution.

According to certain embodiments, for example, the cell extract may comprise a bacterial extract, a yeast extract, a fungal extract, an archaeal extract, a plant cell extract, a mammalian cell extract, an insect cell extract, any extract from cells, any combination of purified proteins for reconstituting protein expression, or any combination thereof. In some embodiments, for instance, the cell extract may comprise an *Escherichia coli* extract, a *Saccharomyces cerevisae* extract, a wheat germ extract, a reticulocyte extract, a HeLa cell extract, a *Spodoptera fruigiperda* extract, a *Trichoplusia ni* extract, or any combination thereof. In further embodiments, for example, the cell extract may comprise an *Escherichia coli* extract.

Figure 11:
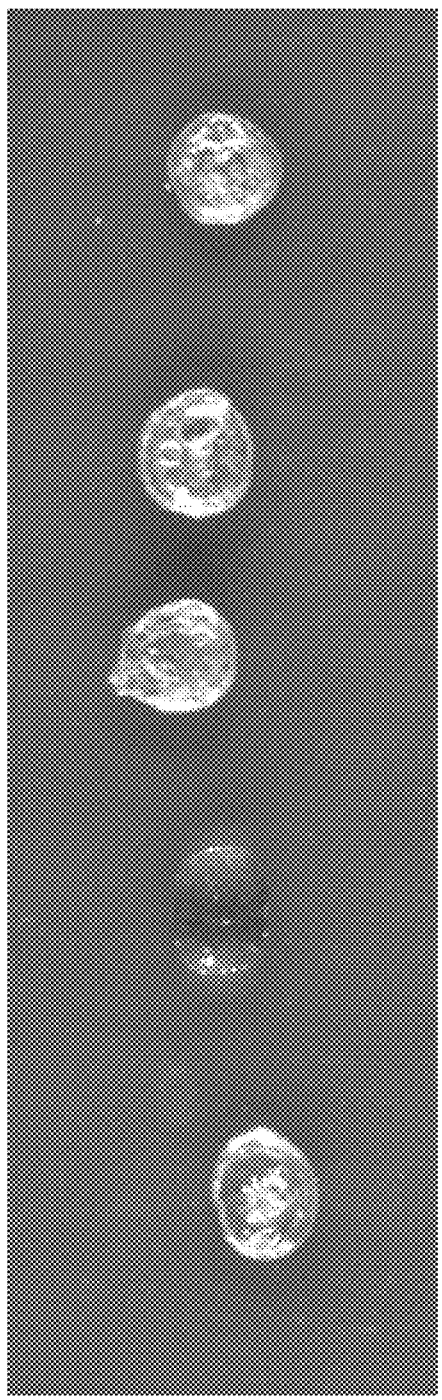
FIG. 11 illustrates products of several different means of preserving cell-free protein expression reaction buffer according to example embodiments.

In accordance with an example embodiment, for instance, the method may be compatible with any chemicals that result in a protected, stabilizing solid to preserve components of the cell-free protein expression system. In some embodiments, for example, non-reducing sugar alcohols having high glass transition temperatures may be used. For example, the first non-reducing sugar alcohol and/or the second non-reducing sugar alcohol may comprise trehalose. In such embodiments, for instance, using trehalose may preserve components of the cell-free protein expression system in an amorphous glass, as illustrated in FIG. 11. Alternatively or in addition, various carbohydrates and polymers may also be used as the first non-reducing sugar alcohol and/or the second non-reducing sugar alcohol. Exemplary embodiments of carbohydrates include, but are not limited to, the following: trehalose, sucrose, lactitol, mannitol, melezitose, raffinose, stachyose, inositol, xylitol, ribitol, iso-maltulose, palatinit, galactitol, arabinitol, glucose, maltose, xylulose, ribose, mannose, fructose, sorbitol, and lactose. Exemplary embodiments of polymers include, but are not limited to, the following: polyethylene glycol (PEG), hydroxyethyl starch, polyvinyl pyrrolidone, polyacrylamide, polyethyleneimine, FICOLL-PAQUE™, dextran, and degraded gelatin. In some embodiments, for example, various combinations of the carbohydrates and polymers may be used.

In accordance with an example embodiment, for instance, preserving the reaction buffer may comprise dissolving the second non-reducing sugar alcohol in the reaction buffer to provide a reaction buffer solution, manipulating the reaction buffer solution to prevent fouling, and drying the reaction buffer solution. In such embodiments, for example, manipulating the reaction buffer solution may comprise at least one of filtering the reaction buffer solution or adding an anti-fouling agent to the reaction buffer solution. In some embodiments and as discussed above, for instance, the anti-fouling agent may comprise an RNAse inhibitor, an antibiotic that does not interfere with transcription or translation, or any combination thereof.

According to certain embodiments, for instance, drying the reaction buffer solution may comprise drying small volume (e.g., 5 μL-35 μL) aliquots on, for example, a silicon sheet at 37° C. In other embodiments, for example, drying the reaction buffer solution may comprise freeze drying the reaction buffer solution. In further embodiments, for instance, drying the reaction buffer solution may comprise spray drying, spray freeze drying, or supercritical drying the reaction buffer solution.

According to certain embodiments, for example, the reaction buffer may comprise nucleotides, amino acids, stabilizing agents, expression enhancing agents, salts, enzymes, or any combination thereof. In some embodiments, for instance, the reaction buffer may comprise at least one stabilizing agent. In such embodiments, for example, stabilizing agents may comprise pH buffers such as 4-(2-hydroxyethyl)-1-piperazineethanesulfonic acid (HEPES) or bis(2-hydroxyethyl)amino-tris(hydroxymethyl)methane (bis-tris). Alternatively or in addition, stabilizing agents may comprise PEG, spermidine, or putrescine. Alternatively or in addition, stabilizing agents may comprise components that improve product folding, stability, and/or function such as chaperones and/or detergents (e.g., BRIJ® 35, digitonin, TRITON™ X100, NONIDET™ P40, octyl glucoside, and/or the like). In further embodiments, for example, the reaction buffer may comprise at least one expression enhancing agent. In such embodiments, for instance, expression enhancing agents may comprise folinic acid, cyclic adenosine monophosphate (cAMP), transfer RNA (tRNA), nicotinamide adenine dinucleotide (NAD+), coenzyme A, oxalic acid, succinic acid, 2-oxoglutaric acid, malic acid, a reducing agent (e.g., dithiothreitol (DTT)), or any combination thereof. In other embodiments, for example, the reaction buffer may comprise nucleotides. In such embodiments, for instance, the nucleotides may comprise adenosine triphosphate (ATP), guanosine-5'-triphosphate (GTP), cytidine triphosphate (CTP), and/or uridine-5'-triphosphate (UTP). In some embodiments, for example, the reaction buffer may contain salts. In such embodiments, for instance, the salts may comprise potassium glutamate, potassium acetate, or ammonium acetate. In some embodiments, for example, the reaction buffer may contain enzymes, for instance, to enable efficient use of an energy source. In such embodiments, the enzyme may be creatine kinase.

According to an example embodiment, the reaction buffer may comprise a magnesium source. Alternatively or in addition, the magnesium source may be preserved separately from the reaction buffer. In such embodiments, for instance, preserving the magnesium source may comprise storing the magnesium source in a dry form or a liquid form. In some embodiments, for example, the magnesium source may comprise magnesium acetate.

In accordance with an example embodiment, for instance, preserving the energy source may comprise storing the energy source in a dry form. In some embodiments, for example, the energy source may comprise creatine phosphate, phosphoenol pyruvate, pyruvate, glutamate, acetyl phosphate, glucose, glucose-6-phosphate, maltodextrin, acetate phosphate, 3-phosphoglycerate, fructose-1,6-bisphosphate, or any combination thereof.

In accordance with an example embodiment, for instance, the method may further comprise reconstituting the cell-free protein expression system. In such embodiments, for example, reconstituting the cell-free protein expression system may occur via adding water to the preserved cell extract, adding water and optionally adding polyethylene glycol (PEG) to the preserved reaction buffer, combining the preserved (and rehydrated) cell extract, the preserved (and rehydrated) reaction buffer, the energy source, the magnesium source, and an expression construct to provide a reconstituted cell-free protein expression system.

According to certain embodiments, for instance, keeping PEG separate from other reaction buffer components during drying may further improve long-term storage of reaction buffer components under heat stress. In such embodiments, for example, PEG may be omitted from final reactions. Alternatively, in other embodiments, for instance, PEG may be stored separately and added upon reconstitution and reaction setup. In further embodiments, for example, optimal PEG concentrations (i.e. intermediate concentrations below 4% (w/v)) may be identified and used in the reaction buffer.

Figure 12:
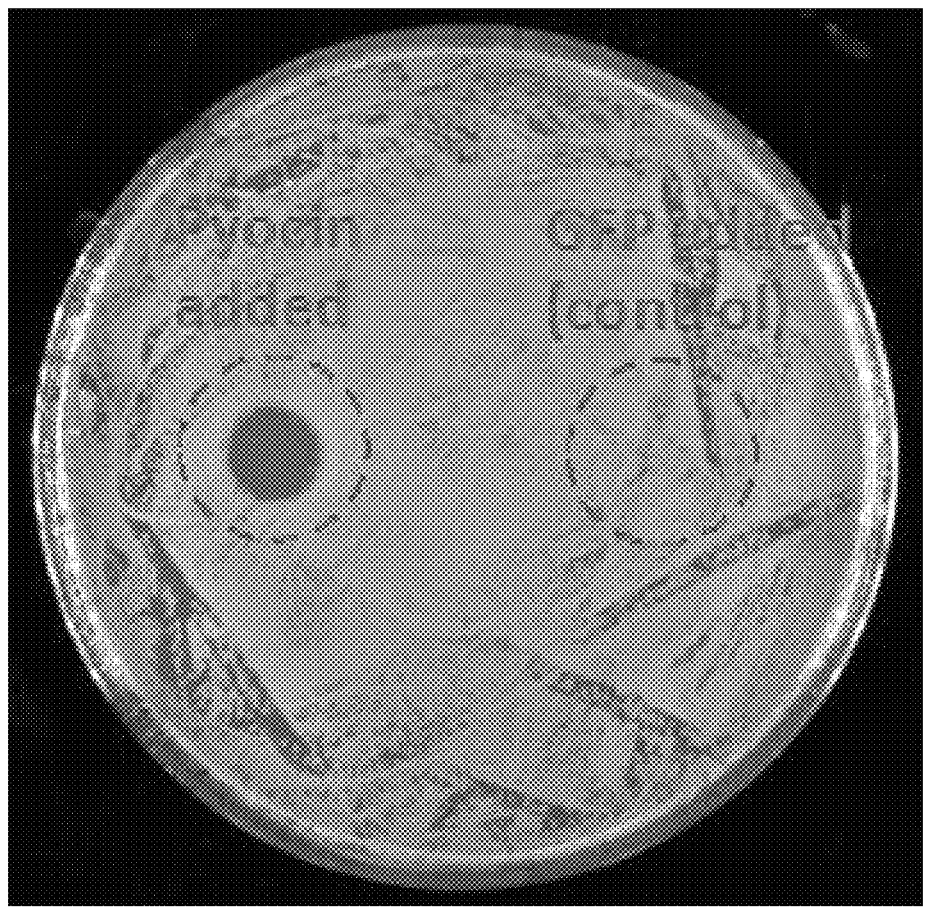
FIG. 12 illustrates the efficacy of preserved cell-free protein expression systems according to an example embodiment.

According to certain embodiments, for instance, the reconstituted cell-free protein expression system may perform both transcription and translation. Accordingly, for example, the reconstituted cell-free protein expression system may produce mRNA from added DNA as well as produce proteins from mRNA. In some embodiments, for instance, the reconstituted cell-free protein expression system may produce a therapeutic capable of killing a pathogen, as illustrated by FIG. 12.

According to certain embodiments, for instance, the reconstituted cell-free protein expression system may be stable under heat stress (e.g., 37° C.) and in a standard/unregulated atmosphere. In some embodiments, for example, the cell-free protein systems may be stable after long-term (i.e. greater than one week) storage, and, as such, may be reconstituted to synthesize proteins.

For example, FIG. 1 illustrates an overview of cell-free protein expression system preservation according to an example embodiment. As shown in FIG. 1, cell-free protein expression system preservation may include preparing a cell-free protein expression system, preserving the cell-free protein expression system, reactivating the cell-free protein expression system and adding DNA, and using the products of the cell-free protein expression system in a wide variety of applications including, but not limited to, forensics, energy applications, on-demand therapeutics, environmental bioremediation, and on-demand biosensing.

Figure 2:
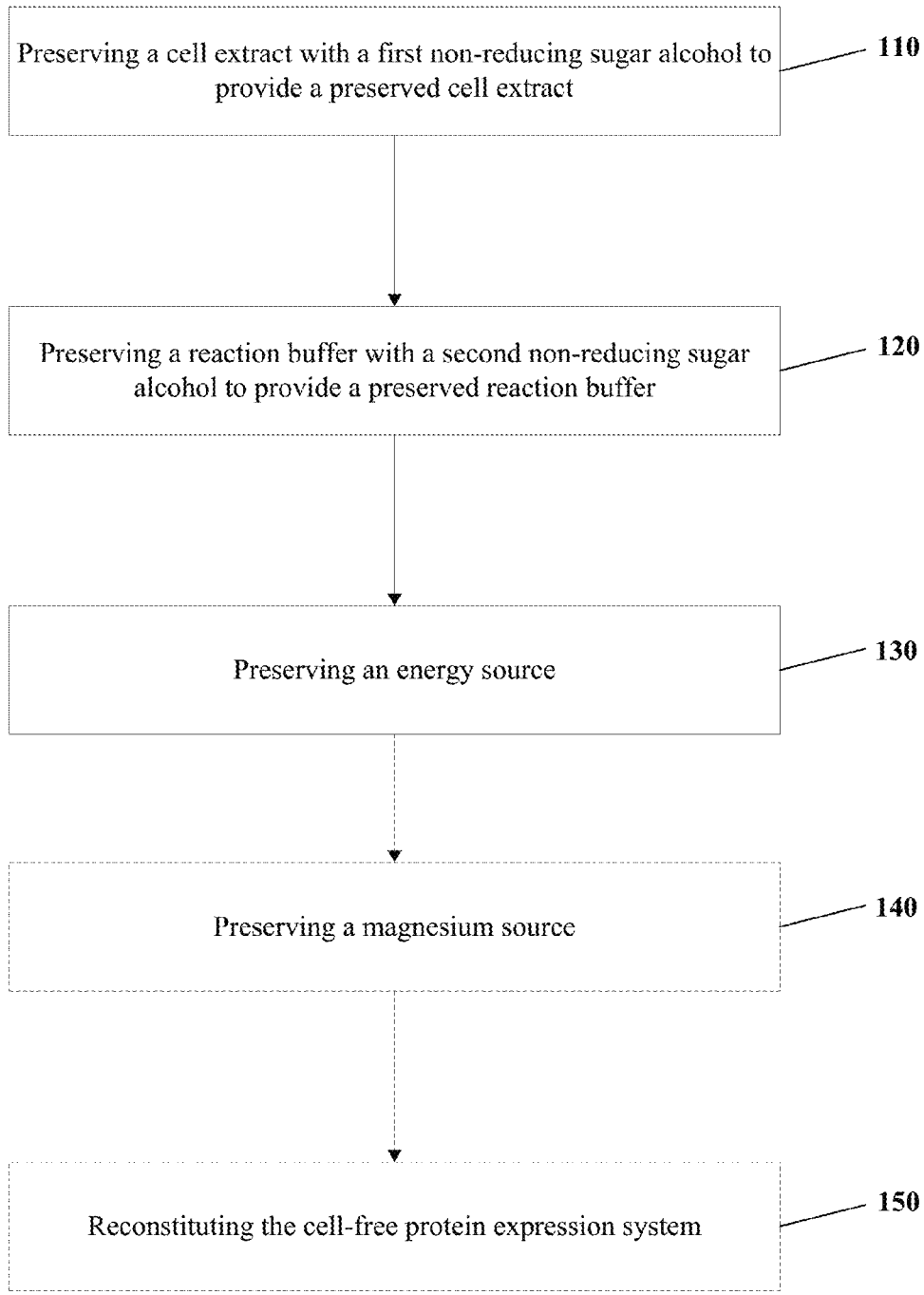
FIG. 2 illustrates a block diagram of a method of preserving a cell-free protein expression system according to an example embodiment.

FIG. 2, for example, illustrates a block diagram of a method of preserving a cell-free protein expression system according to an example embodiment. As shown in FIG. 2, the method comprises preserving a cell extract with a first non-reducing sugar alcohol to provide a preserved cell extract at operation 110. The method further comprises preserving a reaction buffer with a second non-reducing sugar alcohol to provide a preserved reaction buffer at operation 120, and preserving an energy source at operation 130. The method may further comprise optional operations 140 and 150, which comprise preserving a magnesium source and reconstituting the cell-free protein expression system, respectively.

Figure 3:
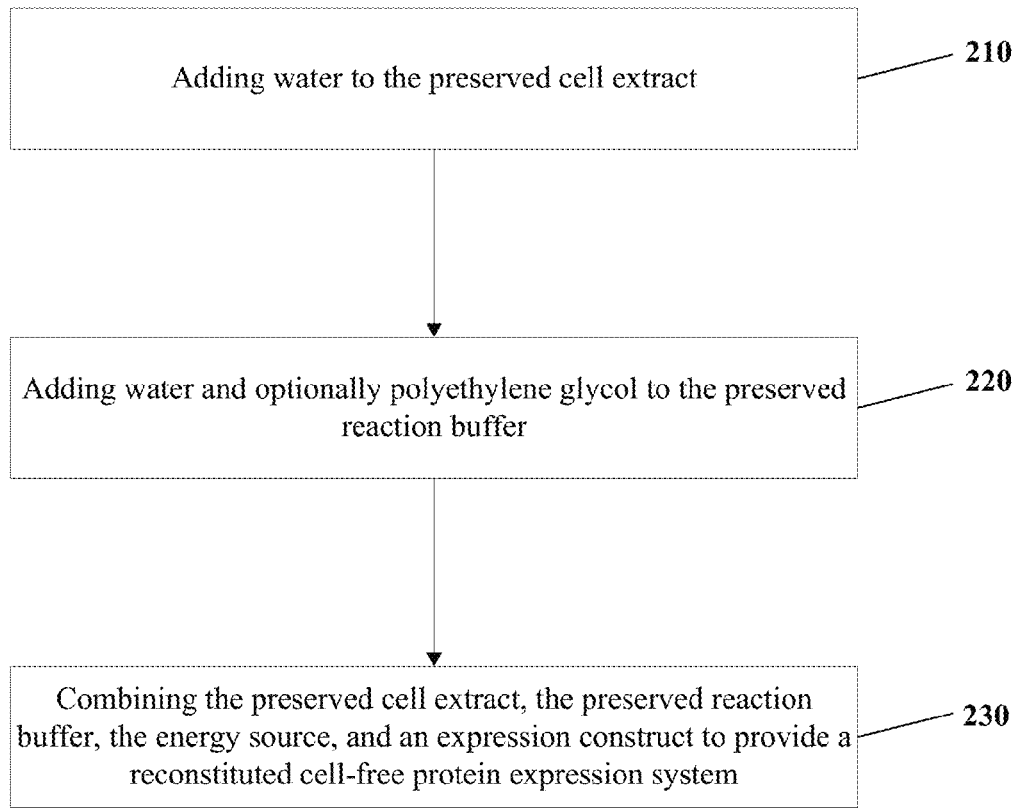
FIG. 3 illustrates a block diagram of a method of reconstituting a cell-free protein expression system according to an example embodiment.

FIG. 3 for example, illustrates a block diagram of a method of reconstituting a cell-free protein expression system according to an example embodiment. As shown in FIG.

3, the method comprises adding water to the preserved cell extract at operation 210. The method further comprises adding water and optionally polyethylene glycol to the preserved reaction buffer at operation 220, and combining the rehydrated cell extract, the rehydrated reaction buffer, the energy source, the magnesium source, and an expression construct to provide a reconstituted cell-free protein expression system at operation 230.

Examples

The present disclosure is further illustrated by the following examples, which in no way should be construed as being limiting. That is, the specific features described in the following examples are merely illustrative, and not limiting.

Cell Extract Preparation

*E. coli* cells (either BL21 STAR™ from INVITROGEN™ or ROSETTA™) were cultured overnight in 100 mL 2×YPTG media in a 500 mL flask at 37° C. in a shaking incubator at 225 RPM. 5 mL of this starter culture was used to inoculate 500 mL 2×YPTG in 2 L flasks at 37° C. and 225 RPM shaking. In order to induce expression of T7 RNA polymerase, cultures were induced with IPTG once the OD600 reached approximately 0.6. Meanwhile, 3 L of 'Buffer A' was prepared in RNAse cleaned glassware and was chilled on ice. Buffer A consisted of 10 mM Tris-acetate buffer (pH 8.2), 14 mM magnesium acetate, 60 mM potassium glutamate, 1 mM dithiothreitol (DTT), and 0.05% 2-mercaptoethanol.

Cells were harvested in mid-log phase by centrifugation at 4000 g for 20 min at 4° C. Wet cell pellet masses were measured. The cells were then washed three times by suspension in 20 mL of Buffer A per gram of wet cells and subsequent centrifugation at 4000 g for 10 min. Following the three washes, cell pellets were weighed again and were stored at −80° C. overnight. The next day, 100 mL of 'Buffer B' was prepared, which consisted of Buffer A without mercaptoethanol, and was chilled on ice. The cell pellets were thawed by placing their containers in room temperature water. Just before the cells were completely thawed, they were transferred to ice to keep the cells below 4° C. The thawed cells were then suspended in 1.27 mL of Buffer B per gram of cell mass. The re-suspended cells were then disrupted by sonication for 10 minutes. The sonicated lysate was centrifuged for 10 minutes at 12,000 g. Supernatants were transferred to fresh centrifuge tubes and again centrifuged for 10 minutes at 12,000 g. Supernatants were again transferred to fresh centrifuge tubes and were centrifuged for 10 minutes at 25,000 g. The final supernatants were transferred to RNAse-free 50 mL conical tubes and were incubated for 30 minutes at 37° C. The extract was then divided into small aliquots and stored at −80° C.

Reaction Buffer Preparation

Reaction buffer was set up as a two-fold concentrated mixture, such that a cell-free expression reaction with 50% reaction buffer would have the following reagents at the specified final concentrations, unless indicated otherwise. Therefore, this reaction buffer solution is referred to as default reaction buffer.

28.5 mM Hepes-KOH (pH 8.2)
1.2 mM ATP
0.85 mM each of CTP, GTP and UTP
2 mM DTT
0.17 mg/mL *E. coli* total tRNA mixture (from strain MRE600)
0.64 mM cAMP
90 mM potassium glutamate
80 mM ammonium acetate
16 mM magnesium acetate
34 μg/mL L-5-formyl-5,6,7,8-tetrahydrofolic acid (folinic acid)
4 mM of cysteine and 2.1 mM of each of 19 other amino acids
2% PEG (8000)
67 mM creatine phosphate (CP)
3.2 μg/mL creatine kinase (CK)

Effect of Non-Reducing Sugar Alcohols

Figure 4:
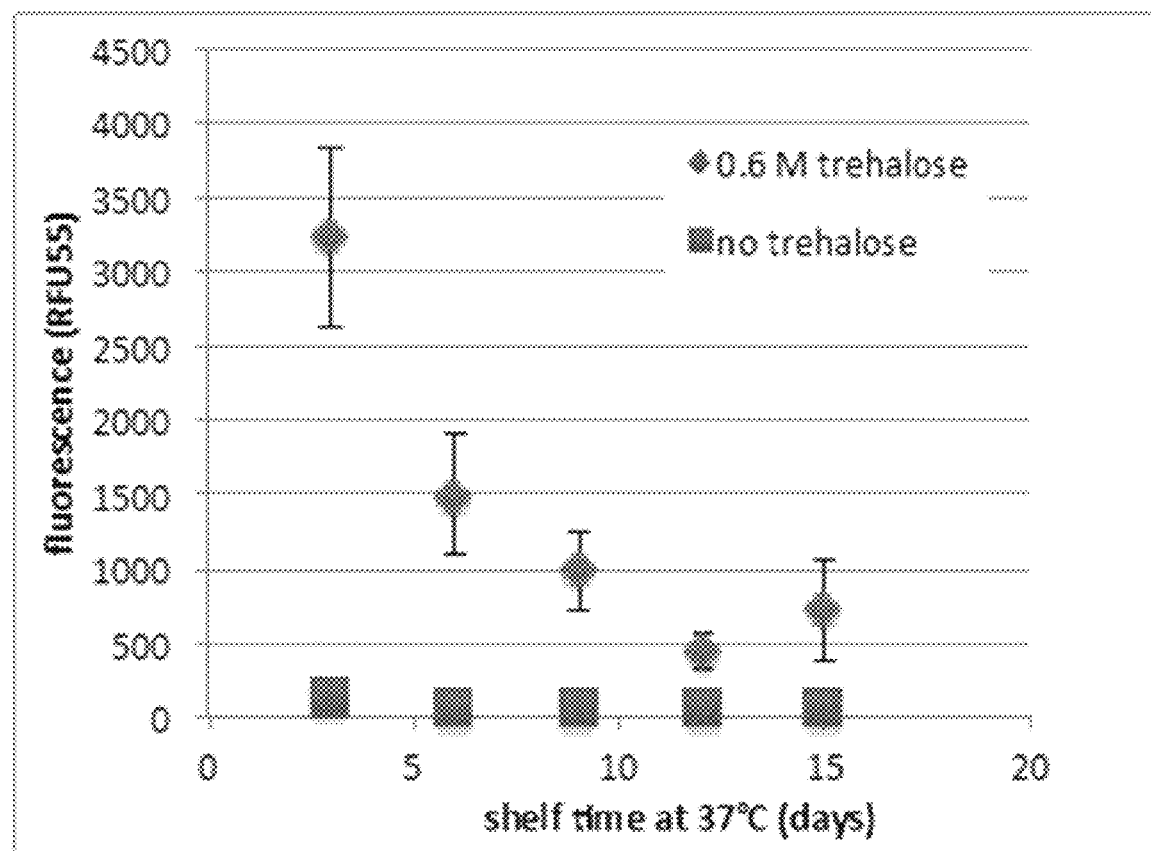
FIG. 4 illustrates the benefit of using non-sugar reducing alcohols according to an example embodiment.

A complete reaction mixture containing everything but DNA (e.g. containing both cell extract and default reaction mixture) was prepared, both with and without 0.6 M trehalose. Drops of 60 μL, of this reaction mixture were dispensed onto wax paper and were dried in a 37° C. incubator. Every 3 days, water was added to reconstitute dried mixtures. To assess expression capacity, triplicates of 20 μL, reactions were set up in a 384 well plate. A DNA plasmid that expresses green fluorescent protein (GFP) from a T7 promoter was added to each well (10 ng/μL final concentration), and 20 μL, of mineral oil was added to each well to prevent evaporation during the expression assay. Reactions were assayed in a Tecan Sapphire II plate reader. FIG. 4 depicts fluorescence resulting from GFP expression after 5 hours of incubation at 35° C.

As illustrated by FIG. 4, without trehalose, protein expression capacity was almost negligible after only 3 days at 37° C. With trehalose, significant expression was observed for over a week, although expression efficiency declined with a half-life of approximately three days. These results clearly show the benefit of non-reducing sugar alcohols such as trehalose.

Cell Extract Preservation 68 ng of trehalose was dissolved in 300 μL, of *E. coli* extract and the resulting solution was filtered using a 0.2 μm spin filter. Drops of 25 μL, of the filtered solution were dispensed onto a silicon sheet and were dried in a 37° C. incubator. Following drying, the cell extracts remained at 37° C. in a standard/unregulated atmosphere. Assays were performed at different time points over approximately three months to quantify protein expression yield after different storage times at 37° C.

Figure 5:
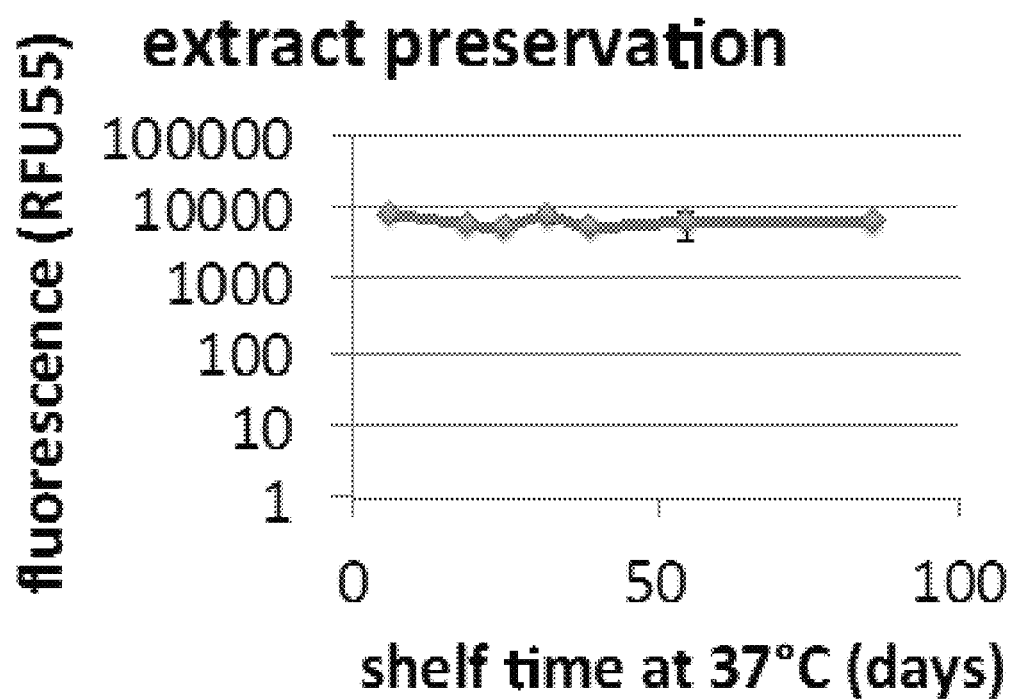
FIG. 5 illustrates the stability of a preserved cell extract system under heat stress according to an example embodiment.

Water was added to reconstitute dried cell extract. Reconstituted cell extract (final 27% v/v), fresh default reaction buffer solution, and a DNA plasmid (final concentration 10 ng/μL) that expresses GFP from a T7 promoter were combined to set up 20 μL reactions in a 384 well plate. 20 μL of mineral oil was added to prevent evaporation, and reactions were assayed in a Tecan Sapphire II plate reader. FIG. 5 depicts fluorescence resulting from GFP expression after 5 hours of incubation at 35° C. The test results, as illustrated in FIG. 5, demonstrate that cell extract can be stabilized for months under heat stress and in a standard/unregulated atmosphere.

Reaction Buffer Preservation

Four different reaction buffer solutions were prepared. Each solution contained default reaction buffer components except for magnesium acetate. In addition, four combinations of potential additives for stabilization were tested: no additives, trehalose (0.6 M), β-cyclodextrine (0.5%), and both trehalose (0.6 M) and β-cyclodextrine (0.5%).

Drops of 35 μL of the filtered solutions were dispensed onto a silicon sheet and were dried in a 37° C. incubator. Following drying, the reaction buffer samples remained at 37° C. In addition, 35 μL of the reaction buffer with no additives were also stored in liquid form at 37° C. Assays were performed at different time points over approximately three months to quantify protein expression yield after different storage times at 37° C. and in a standard/unregulated atmosphere.

Figure 6:
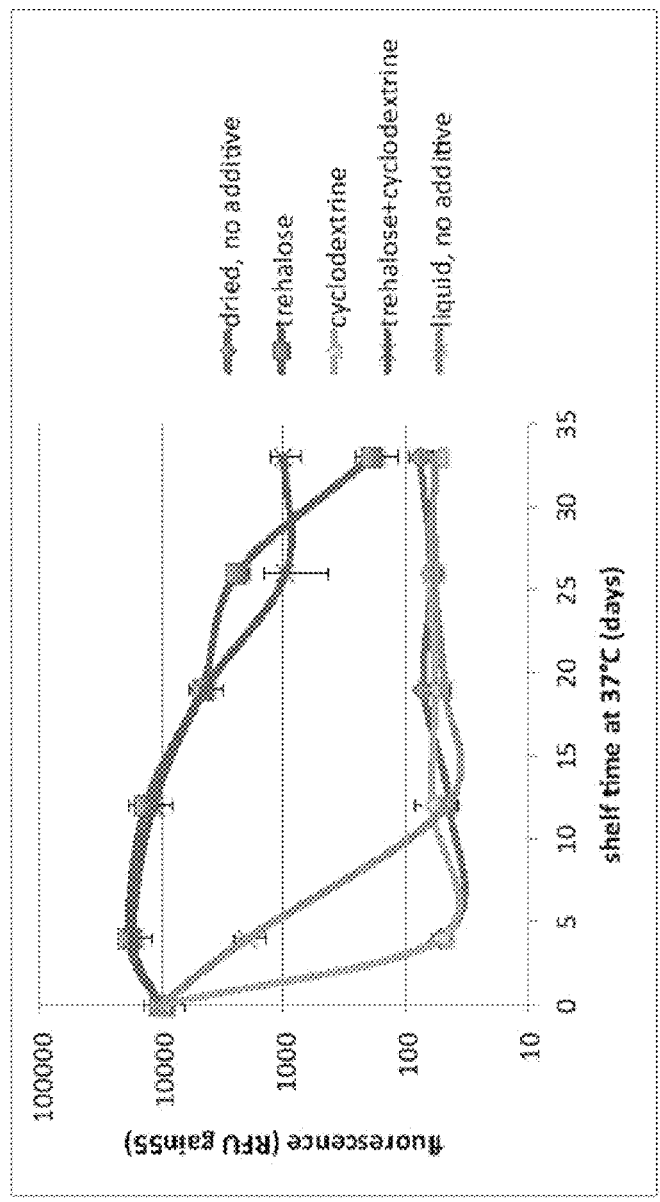
FIG. 6 illustrates the stability of a preserved cell-free protein expression reaction buffer using different additives for stabilization under heat stress according to an example embodiment.

Water was added to reconstitute dried reaction buffer solutions. Fresh cell extract (27% v/v final concentration), reaction buffer, magnesium acetate (16 mM final concentration), and a DNA plasmid (final concentration 10 ng/μL) that expresses GFP from a T7 promoter were combined to set up 20 μL reactions in a 384 well plate. 20 μL of mineral oil was added to prevent evaporation, and reactions were assayed in a Tecan Sapphire II plate reader. FIG. 6 depicts fluorescence resulting from GFP expression after 5 hours of incubation at 35° C.

The two samples that were dried with trehalose (with and without β-cyclodextrin) exhibited strong expression over several weeks at 37° C., as illustrated by FIG. 6. This was a significant improvement compared to the case in which reaction buffer was preserved together with cell extract. However, while stabilization was observed for weeks in this experiment, a clear decline in expression capacity was observed over a month.

Energy Source Separation

Four different variants of default reaction buffer were prepared: without magnesium acetate, with neither magnesium acetate nor creatine phosphate, with neither magnesium acetate nor creatine kinase, and with neither magnesium acetate nor nucleotide triphosphates nor creatine phosphate. Trehalose was added to each reaction buffer variant at a final concentration of 0.6 M, and 38.5 μL droplets were dried on a silicon sheet at 37° C. in an incubator. Prior to drying, an initial baseline experiment was conducted. The following components were combined to set up 20 μL reactions in a 384 well plate: cell extract (27% v/v final concentration), reaction buffer variants (all with trehalose), components omitted from each of the reaction buffer variants, and a DNA plasmid (final concentration 10 ng/μL) that expresses GFP from a T7 promoter. 20 μL of mineral oil was added to prevent evaporation, and reactions were assayed in a Tecan Sapphire II plate reader.

Figure 7:
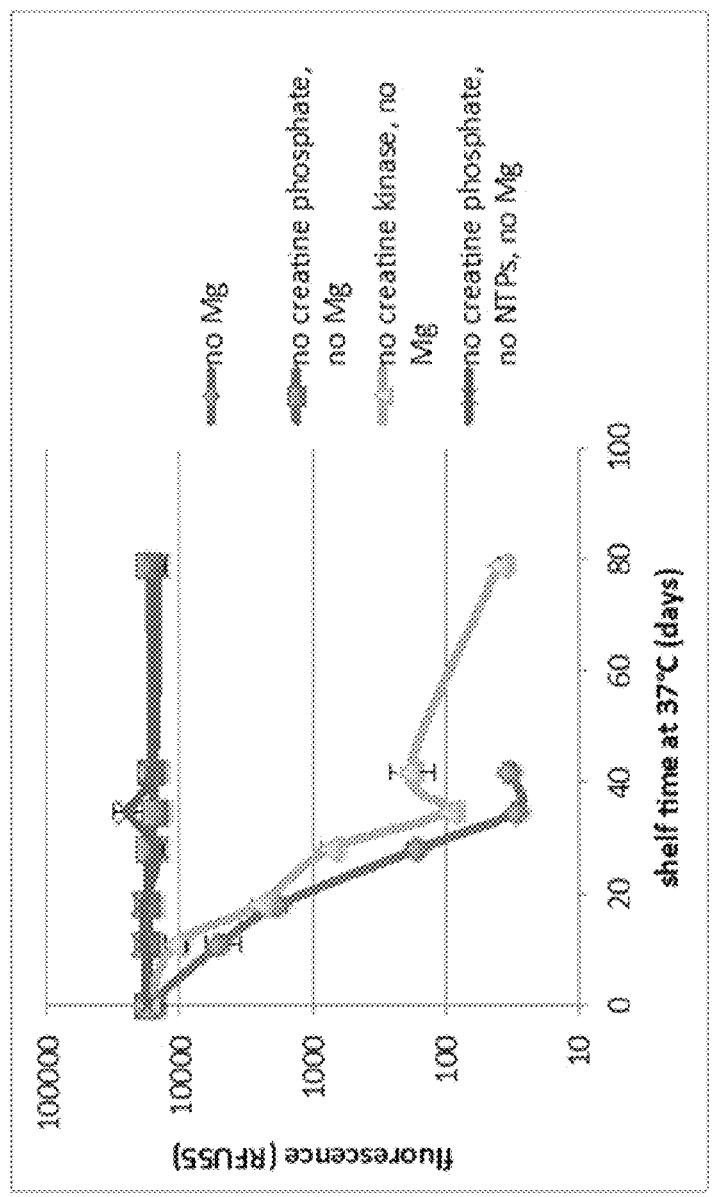
FIG. 7 illustrates the stability of a preserved cell-free protein expression reaction buffer variants under heat stress according to an example embodiment.

After drying, at the time points illustrated in FIG. 7, dried buffer variants were reconstituted by adding water. Fresh cell extract (final 27% v/v), reconstituted reaction buffer solution, fresh components to complement reagents omitted from drying, and a DNA plasmid (final concentration 10 ng/μL) that expresses GFP from a T7 promoter were combined to set up 20 μL reactions in a 384 well plate. 20 μL of mineral oil was added to prevent evaporation, and reactions were assayed in a Tecan Sapphire II plate reader.

FIG. 7 depicts fluorescence resulting from GFP expression after 5 hours of incubation at 35° C. FIG. 7 illustrates a clear improvement resulting from separating the energy source, creatine phosphate, from other reaction buffer components during drying. Even after almost 80 days, final expression yield, as assessed by GFP measurement, was comparable to the initial baseline results.

Additional tests were conducted to examine the stability of creatine phosphate in its original dry form and creatine phosphate mixed with trehalose in liquid form and dried. As such, two variants of default reaction buffer with 0.6 M trehalose were prepared and filtered: one without creatine phosphate and one without magnesium acetate. Aliquots of reaction buffer without creatine phosphate were stored at −80° C., while 20 μL drops of reaction buffer solution without magnesium acetate were dried in on silicon at 37° C. Creatine phosphate in dry powder form was stored at 37° C. In addition, 5 μL, drops of creatine phosphate (1.5 M) mixed with trehalose (0.6 M) were dried on silicon at 37° C. and also stored at 37° C.

Figure 8:
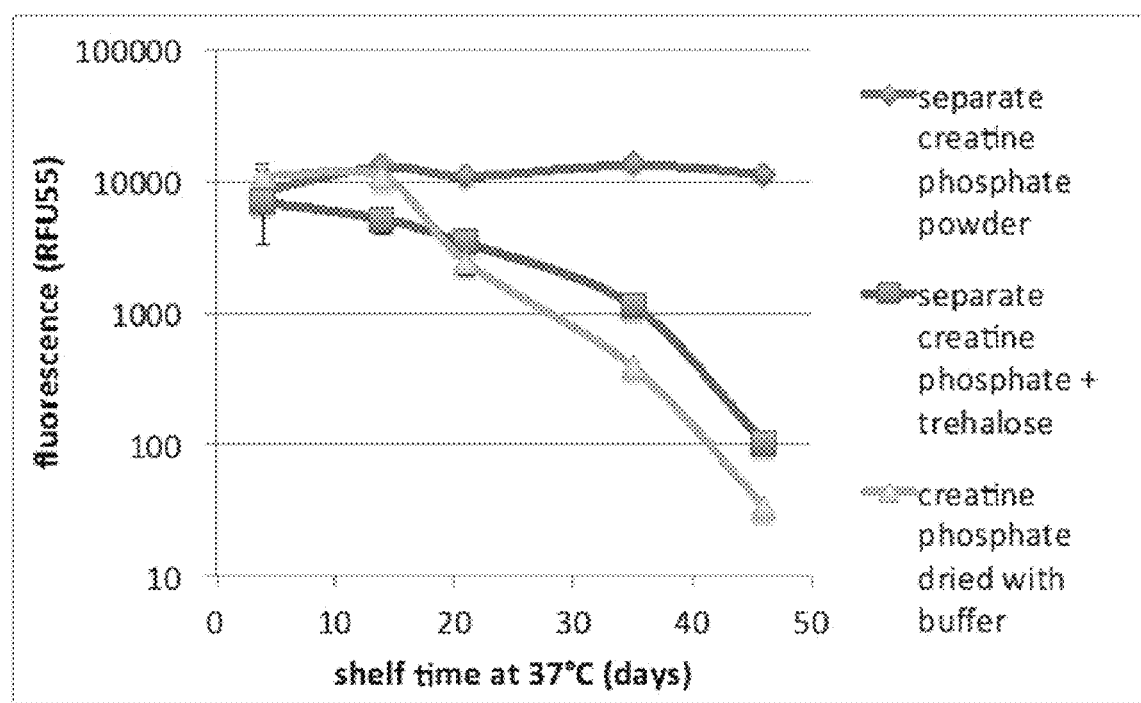
FIG. 8 illustrates the stability of a preserved cell-free protein expression energy source under heat stress according to an example embodiment.

At each time point illustrated in FIG. 8, three protein expression reactions were prepared. In one reaction, cell extract (27% v/v final concentration), dried creatine phosphate stored at 37° C. (67 mM final concentration), an aliquot of the reaction buffer that was prepared without creatine phosphate, and a plasmid (final concentration 10 ng/μL) that expresses GFP from a T7 promoter were combined. In a second reaction, cell extract (27% v/v final concentration), creatine phosphate dried with trehalose 37° C. (67 mM final concentration), an aliquot of the reaction buffer that was prepared without creatine phosphate, and a plasmid (final concentration 10 ng/μL) that expresses GFP from a T7 promoter were combined. In a third reaction, cell extract (27% v/v final concentration), reconstituted reaction buffer without magnesium acetate, magnesium acetate (16 mM final concentration), and a plasmid (final concentration 10 ng/μL) that expresses GFP from a T7 promoter were combined. Triplicate 20 μL, reactions of each type were set up in a 384 well plate. 20 μL, of mineral oil was added to prevent evaporation, and reactions were assayed in a Tecan Sapphire II plate reader. FIG. 8 depicts fluorescence resulting from GFP expression after 5 hours of incubation at 35° C. As shown in FIG. 8, no decrease in protein expression yield was observed over the 46 day duration of the experiment for the sample in which dry creatine phosphate powder was stored at 37° C. This indicates that creatine phosphate may be stored as a dry powder separately from other reaction buffer components and can withstand long term exposure to heat stress in a standard/unregulated atmosphere.

Simultaneous Preservation of Cell-Free Protein Expression System Components

First, the cell extract was dried. Trehalose was added to *E. coli* extract to a final concentration of 0.6 M, and the resulting solution was filtered using a 0.2 μm spin filter. Drops of 25 μL, of the filtered solution were dispensed onto a silicon sheet and were dried in a 37° C. incubator. Second, the reaction buffer components were preserved. Default reaction buffer without magnesium acetate or creatine phosphate was prepared, and trehalose was added to a concentration of 0.6 M. The resulting solution was filtered using a 0.2 μm spin filter. Then, drops of 29.35 μL, of the filtered solutions were dispensed onto a silicon sheet and were dried in a 37° C. incubator. Samples of creatine phosphate in dry form were stored at 37° C., and magnesium acetate was stored in liquid form at 37° C. for the duration of the time course experiment. Magnesium acetate was stored in liquid form simply due to the small scale of this experiment. In larger scale operations, the dried form could be used if desired.

Figure 9:
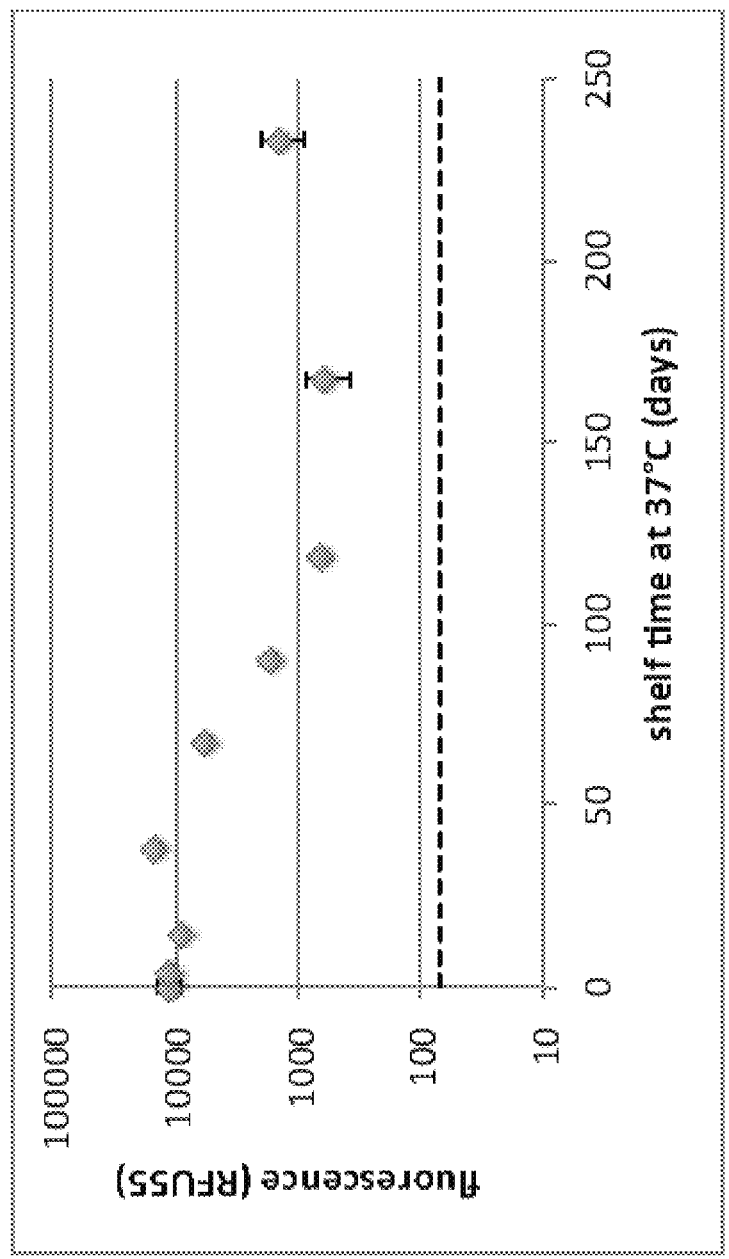
FIG. 9 illustrates the stability of a preserved complete cell-free protein expression system under heat stress according to an example embodiment.

Assays were performed at different time points over approximately eight months to quantify protein expression yield after different storage times at 37° C. in a standard/unregulated atmosphere. Water was added to reconstitute the dried cell extract and the dried reaction buffer. Reconstituted cell extract (27% v/v final concentration), reconstituted reaction buffer solution, magnesium acetate (16 mM final concentration), creatine phosphate (67 mM final concentration), and a DNA plasmid (final concentration 10 ng/μL) that expresses GFP from a T7 promoter were combined to set up 20 μL reactions in a 384 well plate. Mineral oil (20 uL) was added to prevent evaporation, and reactions were assayed using a Tecan Sapphire II plate reader. FIG. 9 depicts fluorescence resulting from GFP expression after 5 hours of incubation at 35° C. Dashed lines indicate the background fluorescence, i.e. fluorescence of a control reaction with no DNA. FIG. 9 illustrates that activity is well preserved for months under heat stress at 37° C. in a standard/unregulated atmosphere, and significant activity above background is still realized even at the end of the almost eight month long experiment. This significantly exceeds the performance of other known preservation methods for cell-free protein expression systems.

Polyethylene Glycol (PEG) Separation

Five variants of reaction buffer were dried in 35 µL drops. Each variant lacked magnesium acetate and creatine phosphate. In addition, the first four variants, lacked amino acids, PEG, DTT, and creatine kinase, respectively. The fifth was a control that only lacked magnesium acetate and creatine phosphate. The five variants are illustrated in order from left to right in FIG. 11. As shown in FIG. 11, omitting PEG from the reaction buffer before drying resulted in a clear, amorphous glass, which is often associated with effective preservation.

Figure 10:
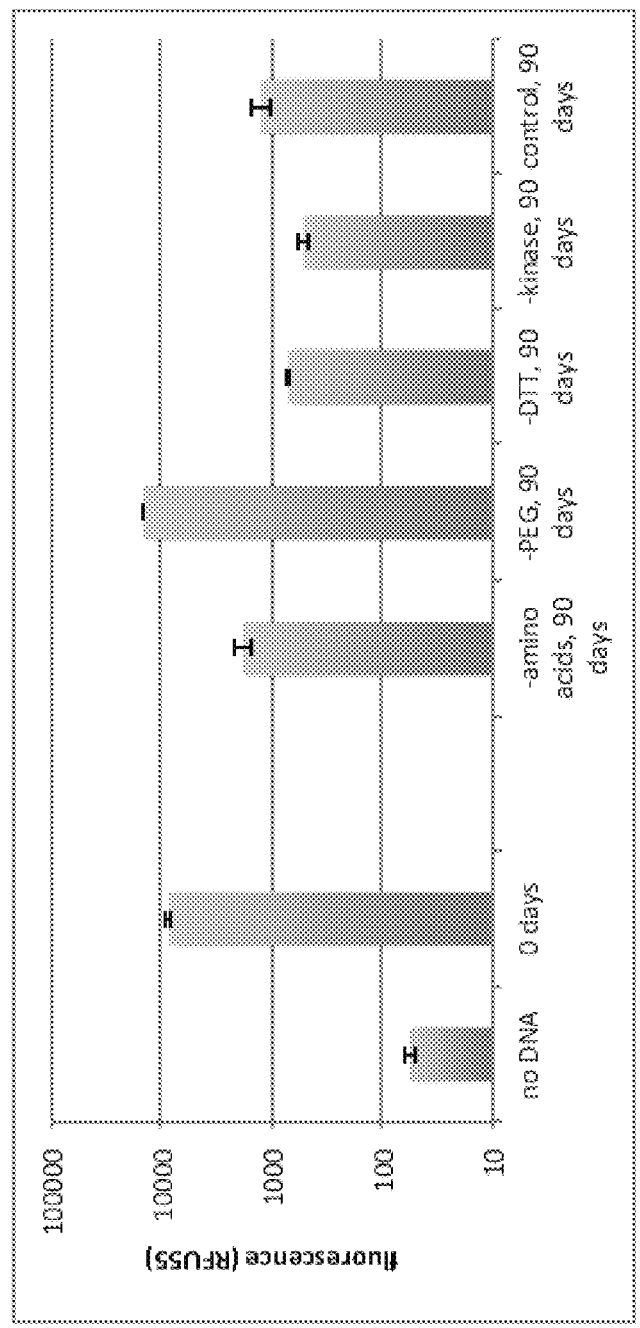
FIG. 10 illustrates the stability of various means of preserving cell-free protein expression reaction buffer according to example embodiments.

Preservation experiments confirmed that omitting PEG from the reaction buffer before drying results in improved preservation. The above dried reaction buffer variants were stored at 37° C. In addition, cell extract was mixed with trehalose (0.6 M) and was dried at 37° C. In order to specifically focus on reaction buffer preservation, the dried extract samples were stored at −80° C., while the reaction buffer samples remained at 37° C. in a standard/unregulated atmosphere. At different time points, protein expression reactions were set up to assess protein expression capacity. Water was added to reconstitute dried cell extract and the dried reaction buffer. Reconstituted cell extract (27% v/v final concentration), reconstituted reaction buffer variants, fresh components missing from the dried reaction buffer variants, and a DNA plasmid (final concentration 10 ng/µL) that expresses GFP from a T7 promoter were combined to set up 20 µL reactions in a 384 well plate. Mineral oil (20 uL) was added to prevent evaporation, and reactions were assayed using a Tecan Sapphire II plate reader. FIG. 10 depicts fluorescence resulting from GFP expression after 5 hours of incubation at 35° C.

FIG. 10 illustrates no dropoff in expression yield after 90 days at 37° C. for the case in which reaction buffer components were dried without PEG. This suggests two possible strategies to further improve long term storage of reaction buffer components under heat stress in a standard/unregulated atmosphere. One strategy is to keep PEG separate from other reaction buffer components during drying. PEG may either be omitted from final reactions, or may alternatively be stored separately and added upon reconstitution and reaction setup. Another strategy is to identify optimal PEG concentrations, i.e. intermediate concentrations below the 4% (w/v) used in the two-fold concentrated reaction buffer solutions.

Exemplary Application

A DNA plasmid (pT7-pyoS5) was constructed to express the pyoS5 gene from *Pseudomonas aeruginosa* PAO1. Specifically, the pyoS5 gene was placed downstream of a T7 promoter and a strong ribosome binding site in a high copy backbone. This construct was expressed using *E. coli* cell-free reagents, and the reaction product was tested for efficacy in killing *P. aeruginosa* without any additional purification or post processing steps. Specifically, *P. aeruginosa* cells of susceptible strain type were first grown in 2 mL casamino acids media (CAA) at 37° C. with shaking at 225 RPM. The next day, the overnight culture was diluted one hundred fold into 2 mL of fresh media. A cell-free reaction mixture was made by mixing 45.9 µL of cell extract with 85 µL of default reaction buffer. This reaction mixture was then filter sterilized with a 0.2 µm spin column. One reaction was set up to express pyoS5, and a second reaction was set up to express green fluorescent protein. For each reaction, 53.9 µL of reaction mixture was combined with 700 ng of the appropriate DNA plasmid in a 1.5 mL microcentrifuge tube, and water was added to bring the final volumes to 70 uL. These tubes were incubated at room temperature in a rotating holder for approximately 5 hours. The *P. aeruginosa* culture, having grown to an OD600 value of approximately 0.6, was diluted to a density of approximately $10^7$ cells/mL. Then, 100 µL of the diluted cell culture was spread on a CAA agarose plate and allowed to dry. A droplet of 5 µL of the cell-free reaction that expressed pyoS5 was dispensed on one side of the plate. As a control, a droplet of 5 µL of the other cell-free reaction that expressed green fluorescent protein was dispensed on the other side of the plate. The plate was then imaged the following day to quantify clearing of cells in the pyoS5 region as illustrated in FIG. 12. This experiment was also repeated with 0.6 M trehalose added to the cell-free expression reaction, and similar killing results were obtained.

Exemplary Embodiments

Having described various aspects and embodiments of the invention herein, further specific embodiments of the invention include those set forth in the following paragraphs.

In some example embodiments, a method of preserving a cell-free protein expression system is provided. In general, the method of preserving a cell-free protein expression system, according to certain example embodiments, includes preserving a cell extract with a first non-reducing sugar alcohol to provide a preserved cell extract, preserving a reaction buffer with a second non-reducing sugar alcohol to provide a preserved reaction buffer, and preserving an energy source, so that the cell extract, the reaction buffer, and the energy source are preserved separately.

In accordance with an example embodiment, preserving the cell extract comprises dissolving the first non-reducing sugar alcohol in the cell extract to provide a cell extract solution, manipulating the cell extract solution to prevent fouling, and drying the cell extract solution. In such embodiments, manipulating the cell extract solution comprises at least one of filtering the cell extract solution or adding an anti-fouling agent to the cell extract solution. In some embodiments, the anti-fouling agent comprises an RNAse inhibitor, an antibiotic that does not interfere with transcription or translation, or any combination thereof.

According to an example embodiment, the cell extract comprises a bacterial extract, a yeast extract, a fungal extract, an archaeal extract, a plant cell extract, a mammalian cell extract, an insect cell extract, any extract from cells, any combination or purified proteins for reconstituting protein expression or any combination thereof. In further embodiments, the cell extract comprises an *Escherichia coli* extract, a *Saccharomyces cerevisae* extract, a wheat germ extract, a reticulocyte extract, a HeLa cell extract, a *Spodoptera fruigiperda* extract, a *Trichoplusia ni* extract, or any combination thereof. According to an example embodiment, the first non-reducing sugar alcohol and/or the second non-reducing sugar comprises trehalose.

In accordance with an example embodiment, preserving the reaction buffer comprises dissolving the second non-reducing sugar alcohol in the reaction buffer to provide a reaction buffer solution, manipulating the reaction buffer solution to prevent fouling, and drying the reaction buffer solution. In such embodiments, manipulating the reaction buffer solution comprises at least one of filtering the reaction buffer solution or adding an anti-fouling agent to the reaction buffer solution. In some embodiments, the anti-fouling agent comprises an RNAse inhibitor, an antibiotic that does not interfere with transcription or translation, or any combination thereof.

According to an example embodiment, the reaction buffer comprises nucleotides, amino acids, stabilizing agents, expression enhancing agents, salts, enzymes, or any combination thereof. In some embodiments, stabilizing agents comprise 4-(2-hydroxyethyl)-1-piperazineethanesulfonic acid, bis(2-hydroxyethyl)amino-tris(hydroxymethyl)methane, polyethylene glycol, spermidine, putrescine, chaperones, detergents, or any combination thereof. In further embodiments, expression enhancing agents comprise folinic acid, cyclic adenosine monophosphate, transfer RNA, nicotinamide adenine dinucleotide, coenzyme A, oxalic acid, succinic acid, 2-oxoglutaric acid, malic acid, a reducing agent, or any combination thereof. In some embodiments, salts comprise potassium glutamate, potassium acetate, or ammonium acetate. In some embodiments, enzymes comprise creatine kinase.

In accordance with an example embodiment, preserving the energy source comprises storing the energy source in a dry form. In some embodiments, the energy source comprises creatine phosphate, phosphoenol pyruvate, pyruvate, glutamate, acetyl phosphate, glucose, glucose-6-phosphate, maltodextrin, acetate phosphate, 3-phosphoglycerate, fructose-1,6-bisphosphate, or any combination thereof. According to an example embodiment, a magnesium source is optionally preserved separately from the reaction buffer. In such embodiments, preserving the magnesium source comprises storing the magnesium source in a dry form or a liquid form. In some embodiments, the magnesium source comprises magnesium acetate.

In accordance with an example embodiment, the method further comprises reconstituting the cell-free protein expression system via adding water to the preserved cell extract, adding water and optionally polyethylene glycol to the preserved reaction buffer, and combining the rehydrated cell extract, the rehydrated reaction buffer, the energy source, and an expression construct to provide a reconstituted cell-free protein expression system. In some embodiments, the reconstituted cell-free protein expression system performs transcription and translation. In certain embodiments, the reconstituted cell-free protein expression system is stable under heat stress in a standard/unregulated atmosphere.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. A method of preserving a cell-free protein expression system, comprising:
    extracting cellular components necessary for protein expression from a whole cell to create a cell extract;
    dissolving trehalose in the cell extract to provide a cell extract solution;
    filtering the cell extract solution or adding a first anti-fouling agent to the cell extract solution to prevent fouling of the cell extract solution;
    preserving the cell extract solution by drying the cell extract solution in an incubator to provide a preserved cell extract, wherein the preserved cell extract is stable for at least three months at 37° C. temperature;
    dissolving trehalose in a reaction buffer to provide a reaction buffer solution;
    filtering the reaction buffer solution or adding a second anti-fouling agent to the reaction buffer solution to prevent fouling of the reaction buffer solution;
    preserving the reaction buffer by drying the reaction buffer solution in an incubator to provide a preserved reaction buffer; and
    storing an energy source in a dry form to provide a preserved energy source,
    wherein the cell extract, the reaction buffer, and the energy source are preserved separately in a dry form and the preserved cell extract, preserved reaction buffer, and preserved energy source are components of the cell-free protein expression system.

2. The method according to claim 1, wherein the first anti-fouling agent or the second anti-fouling agent comprises an RNAse inhibitor or an antibiotic.

3. The method according to claim 1, wherein the cell extract is a bacterial cell extract, a yeast cell extract, a fungal cell extract, an archaeal cell extract, a plant cell extract, a mammalian cell extract, an insect cell extract, or a combination of purified proteins.

4. The method of claim 1, wherein the cell extract is an *Escherichia coli* cell extract, a *Saccharomyces cerevisae* cell extract, a wheat germ cell extract, a reticulocyte cell extract, a HeLa cell extract, a *Spodoptera fruigiperda* cell extract, or a *Trichoplusia ni* cell extract.

5. The method of claim 1, wherein the reaction buffer further comprises one or more stabilizing agents, expression enhancing agents, salts, enzymes, or any combination thereof.

6. The method of claim 5, wherein the stabilizing agent is 4-(2-hydroxyethyl)-1-piperazineethanesulfonic acid, bis(2-hydroxyethyl)amino-tris(hydroxymethyl)methane, polyethylene glycol, spermidine, putrescine, a chaperon, a detergent, or any combination thereof.

7. The method of claim 1, wherein the energy source is at least one of: creatine phosphate, phosphoenol pyruvate, pyruvate, glutamate, acetyl phosphate, glucose, glucose-6-phosphate, maltodextrin, acetate phosphate, 3-phosphoglycerate, fructose-1, 6-bisphosphate.

8. The method of claim 1, further comprising reconstituting the cell-free protein expression system via:
    adding water to the preserved cell extract to create a rehydrated cell extract;
    adding water to the preserved reaction buffer to create a rehydrated reaction buffer; and
    combining the rehydrated cell extract, the rehydrated reaction buffer, the preserved energy source, and an expression construct to provide a reconstituted cell-free protein expression system.

9. The method according to claim 8, wherein the reconstituted cell-free protein expression system performs transcription and translation.

10. The method according to claim 8, wherein the reconstituted cell-free protein expression system is stable at 37° C. in a standard atmosphere and without oxygen control or humidity control.

11. The method of claim 1, wherein the reaction buffer solution comprises at least one of: adenosine triphosphate (ATP), guanosine-5'-triphosphate (GTP), cytidine triphosphate (CTP), or uridine-5'-triphosphate (UTP).

12. The method of claim 1, wherein drying the cell extract solution further comprises drying aliquots of the cell extract solution on a sheet in the incubator at 37° C., wherein the aliquots of the cell extract solution range in volume from 5 µL-35 µL.

13. The method of claim 1 further comprising:
  storing the preserved cell extract and the preserved reaction buffer for eight months;
  reconstituting the preserved cell extract and preserved reaction buffer with water;
  combining the reconstituted cell extract at a final concentration of 27% v/v, the reconstituted reaction buffer, an amount of magnesium acetate at a final concentration of 16 mM, and an amount of creatine phosphate at a final concentration of 67 mM to create a solution; and
  expressing mRNA or proteins when the solution is combined with a DNA molecule that codes for the production of mRNA or proteins in the presence of transcription or translation machinery.

* * * * *